(12) United States Patent
Choi et al.

(10) Patent No.: US 10,119,142 B2
(45) Date of Patent: Nov. 6, 2018

(54) PHARMACEUTICAL COMPOSITION FOR TREATING CHARCOT MARIE TOOTH DISEASE

(71) Applicant: SAMSUNG LIFE PUBLIC WELFARE FOUNDATION, Yongsan-gu (KR)

(72) Inventors: Byung-Ok Choi, Seoul (KR); Young Bin Hong, Seoul (KR)

(73) Assignee: SAMSUNG LIFE PUBLIC WELFARE FOUNDATION, Seoul (KR)

(*) Notice: Subject to any disclaimer, the term of this patent is extended or adjusted under 35 U.S.C. 154(b) by 0 days.

(21) Appl. No.: 15/690,478

(22) Filed: Aug. 30, 2017

(65) Prior Publication Data

US 2018/0066257 A1     Mar. 8, 2018

(30) Foreign Application Priority Data

Sep. 5, 2016 (KR) ........................ 10-2016-0114009

(51) Int. Cl.
| | | |
|---|---|---|
| C12N 15/113 | (2010.01) | |
| A61K 9/127 | (2006.01) | |
| A61K 31/713 | (2006.01) | |
| C12N 15/11 | (2006.01) | |

(52) U.S. Cl.
CPC .......... *C12N 15/113* (2013.01); *A61K 9/1272* (2013.01); *A61K 31/713* (2013.01); *C12N 15/11* (2013.01); *C12N 15/1138* (2013.01); *C12N 2310/14* (2013.01); *C12N 2320/34* (2013.01)

(58) Field of Classification Search
CPC .......................... C12N 15/113; A01K 2207/05
See application file for complete search history.

(56) References Cited

U.S. PATENT DOCUMENTS

2013/0197061 A1* 8/2013 Hohjoh .............. A61K 31/7105
                                                             514/44 A

OTHER PUBLICATIONS

Valentijn et all. Nature Genetics 2, 288-291 (Year: 1992).*
English Translation on Mar. 2018 of the Office action dated Oct. 12, 2017 from the Korean Patent Office Korean application 10-2016-0114009, pp. 1-14. (Year: 2018).*
Hara, et al. (2014) "Rer1 and calnexin regulate endoplasmic reticulum retention of a peripheral myelin protein 22 mutant that causes type 1A Charcot-Marie-Tooth disease", Scientific Reports, vol. 11, No. 4:6992.
Office Action dated Oct. 12, 2017 from the Korean Patent Office in respect of the corresponding Korean Patent Application—not in English language.
Ji-Su Lee, et al.; "Allele-Specific SIRNA Ameliorates Pheno-Typic Severity in PMP22 Mutation Bearing Mouse"; Brain Conference 2015, Joint Conference of KSBNS and KSND, Sep. 11-12, 2015; p. 229.
Ji-Su Lee, et al.: "Allele-Specific SIRNA Ameliorates Phenotypic Severity in PMP22 Mutation Bearing Mouse"; The 4th International Conference on Molecular Neurodegeneration, ICMN 2016: Novel Systems and Emerging Concepts, May 9-11, 2016.

* cited by examiner

*Primary Examiner* — Brian A Whiteman
(74) *Attorney, Agent, or Firm* — Harness, Dickey & Pierce, P.L.C.

(57) ABSTRACT

An siRNA for specifically targeting a PMP22 mutant gene and a pharmaceutical composition for preventing or treating Charcot Marie Tooth disease, which includes the same, are provided. According to the present invention, it is confirmed that selective suppression of a PMP22 mutant allele by a non-viral delivery system of siRNA may improve demyelinating neuropathic symptoms of CMT in vivo, enhance a motor ability and increase a volume of muscle. Therefore, the siRNA may be used in a useful method for treating various dominantly inherited peripheral neuropathies including CMT.

12 Claims, 14 Drawing Sheets

Specification includes a Sequence Listing.

PHARMACEUTICAL COMPOSITION FOR TREATING CHARCOT MARIE TOOTH DISEASE

CROSS-REFERENCE TO RELATED APPLICATION

This application claims priority to and the benefit of Korean Patent Application No. 10-2016-0114009, filed on Sep. 5, 2016, the disclosure of which is incorporated herein by reference in its entirety.

FIELD

The present invention relates to a small interfering RNA (siRNA) for specifically targeting a PMP22 mutant gene and a pharmaceutical composition for preventing or treating Charcot Marie Tooth disease including the same.

BACKGROUND

Inherited peripheral neuropathy (IPN) is a genetically and clinically heterogeneous group of disorders encompassing Charcot Marie Tooth disease (CMT; also termed hereditary motor and sensory neuropathy, HMSN), hereditary neuropathy with liability to pressure palsy (HNPP), hereditary motor neuropathy (HMN), and hereditary sensory and autonomic neuropathy (HSAN). Among these, the CMT is the most commonly occurring IPN with a frequency of 1 in 2,500 people. The characteristic clinical features of CMT are symmetrical distal polyneuropathy, such as distal wasting, weakness, foot deformities, and slowly-progressing sensory loss in the lower limbs.

More than 80 relevant genes causing CMT have been isolated. Among these, the most frequent CMT-causative genes include peripheral myelin protein 22 (PMP22), myelin protein zero (MPZ), gap junction protein beta 1 (GJB1), and mitofusin 2 (MFN2), which account for approximately 90% of the CMT cases. These genes cause disease in an autosomal dominant or X-linked dominant manner. Over 95% of the CMT cases are dominantly inherited, whereas very few cases are inherited in an autosomal recessive or X-linked recessive manner. Although the majority of the autosomal dominant cases are caused by duplication of a PMP22 gene, more than 50% of the cases are caused by point mutations in 40 or more genes.

Clinically applicable methods of treating genetically recessive diseases include gene therapy, enzyme replacement, and cell transplantation. However, these clinical approaches are limited in autosomal dominant cases, which are caused by gain-of-function mutations of mutant proteins. Although various strategies have been proposed to bypass the detrimental effect of the mutant proteins, fundamental therapeutic methods should be based on the suppression or the removal of mutant alleles or proteins.

Meanwhile, as small interfering RNA (siRNA) targets a specific sequence of a gene, modulating the specificity of siRNA to the mutant alleles is considered to be theoretically feasible gene therapy. Indeed, it was reported that, when mutant allele-specific short hairpin RNA (shRNA) is administered via a viral delivery system, the mutant allele-specific shRNA has a therapeutic effect on various disease models including Alzheimer's disease, Parkinson's disease, Huntington's disease, Machado-Joseph disease, and amyotrophic lateral sclerosis.

SUMMARY

Accordingly, the present inventors have conducted intensive research to investigate the therapeutic feasibility of non-viral delivery of siRNA specifically targeting autosomal dominant mutant alleles involved in CMT, and found that the siRNA having a specific sequence which suppresses expression of a Pmp22 mutant allele enhances both motor function and nerve physiology. Therefore, the present invention has been completed based on these facts.

Therefore, an aspect of the present disclosure is to provide a small interfering RNA (siRNA) for specifically targeting a Pmp22 mutant gene, a pharmaceutical composition for preventing or treating Charcot Marie Tooth disease including the same, and a prophylactic/therapeutic method using the same.

However, the technical objects of the present disclosure are not limited thereto, and other objects of the present invention which are not disclosed herein will become more apparent to those of ordinary skill in the art by describing in detail exemplary embodiments thereof.

According to an aspect of the present disclosure, there is provided a pharmaceutical composition for preventing or treating Charcot Marie Tooth disease, which includes an expression inhibitor of a peripheral myelin protein 22 (Pmp22) mutant gene as an active ingredient.

According to another aspect of the present disclosure, there is provided a method of preventing or treating Charcot Marie Tooth disease, which includes administering an expression inhibitor of a Pmp22 mutant gene to a subject.

According to still another aspect of the present disclosure, there is provided a use of the expression inhibitor of the Pmp22 mutant gene to prevent or treat Charcot Marie Tooth disease.

According to one exemplary embodiment of the present disclosure, the Pmp22 mutant gene may be characterized by thymine, which is a base at position 47 of a wild-type Pmp22 gene, being replaced with cytosine.

According to another exemplary embodiment of the present disclosure, the Pmp22 mutant gene may consist of a base sequence set forth in SEQ ID NO: 1.

According to still another exemplary embodiment of the present disclosure, the expression inhibitor may be a small interfering RNA (siRNA), a short hairpin RNA (shRNA), or an aptamer, which specifically binds to the Pmp22 mutant gene.

According to yet another exemplary embodiment of the present disclosure, the siRNA may have a sense strand consisting of a base sequence set forth in SEQ ID NO: 2, 3 or 4 and an antisense strand consisting of a sequence complementary to the sense strand.

According to yet another exemplary embodiment of the present disclosure, the composition may further include a lipid polymer as an siRNA delivery system.

According to yet another aspect of the present disclosure, there is provided an siRNA which consists of a base sequence set forth in SEQ ID NO: 2, 3 or 4 and an antisense strand consisting of a sequence complementary to the sense strand and binds to a Pmp22 mutant gene to suppress expression of the Pmp22 mutant gene.

According to one exemplary embodiment of the present disclosure, the Pmp22 mutant gene may be characterized by thymine, which is a base at position 47 of a wild-type Pmp22 gene, being replaced with cytosine.

According to another exemplary embodiment of the present disclosure, the Pmp22 mutant gene may consist of a base sequence set forth in SEQ ID NO: 1.

According to yet another aspect of the present disclosure, there is provided a recombinant vector including the siRNA.

According to yet another aspect of the present disclosure, there is provided a pharmaceutical preparation for preventing or treating Charcot Marie Tooth disease, which includes the siRNA.

According to yet another aspect of the present disclosure, there is provided a method of suppressing expression of a target gene in cells, which includes introducing the siRNA into the cells in vitro.

According to one exemplary embodiment of the present disclosure, the target gene may be a Pmp22 mutant gene.

According to another exemplary embodiment of the present disclosure, the Pmp22 mutant gene may consist of a base sequence set forth in SEQ ID NO: 1.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Figure 1:
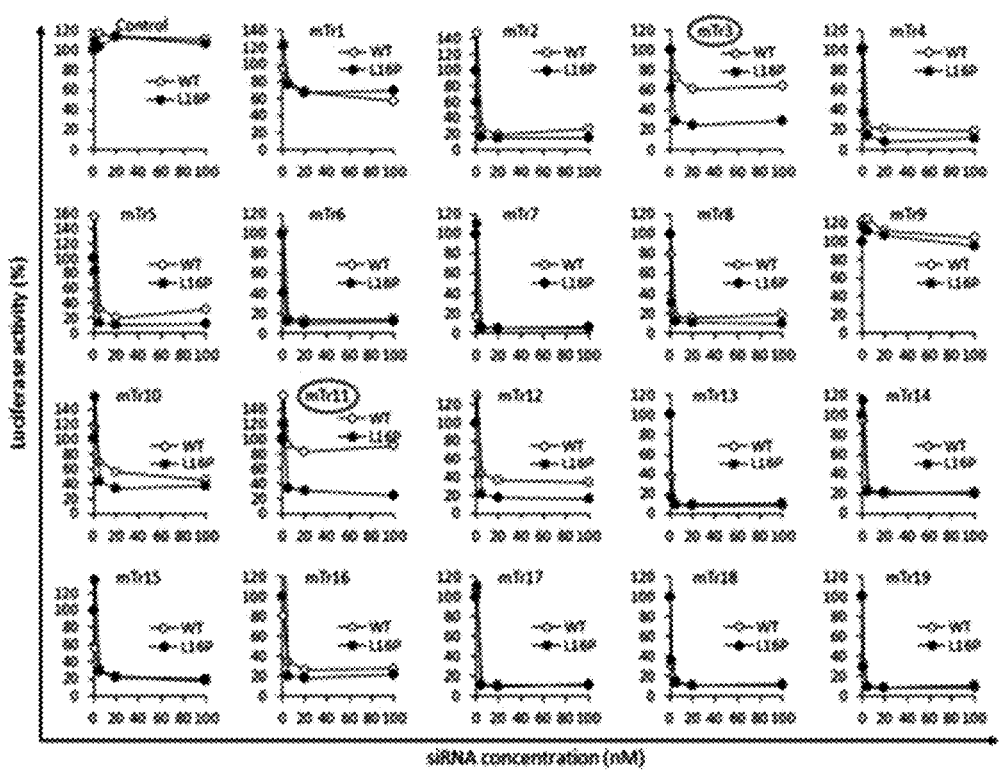
FIG. 1 shows results obtained by performing a dual-luciferase assay on 19 siRNAs to screen siRNAs specific to a mouse Pmp22-L16P mutant gene.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclature used in this specification and the experimental methods described below are widely known and generally used in the related art.

The present invention provides a pharmaceutical composition for preventing or treating Charcot Marie Tooth disease (CMT), which includes an expression inhibitor of a peripheral myelin protein 22 (PMP22) mutant gene.

In the present invention, a human Pmp22 mutant gene is characterized by thymine, which is a base at a position 47 of a human wild-type PMP22 (NCBI Accession No. NM_000304.2) sequence, being replaced with cytosine, and preferably consists of a base sequence set forth in SEQ ID NO: 1.

In the present invention, the term "suppression of expression" refers to a situation causing a decline in the function of a target gene, preferably means that a target gene is expressed at an undetectable or insignificant level through the suppression of expression of the target gene.

In the present invention, the term "expression inhibitor" includes siRNA, shRNA, microRNA, an antisense oligonucleotide, PNA, an aptamer, etc., but the present invention is not limited thereto. Preferably, the expression inhibitor is siRNA.

In the present invention, the term "siRNA" refers to a short double-stranded RNA that may induce RNA interference (RNAi) through cleavage of certain mRNA. In this case, the siRNA consists of a sense RNA strand having a sequence homologous to mRNA of a target gene and an antisense RNA strand having a sequence complementary to the sense RNA strand. Because the siRNA may inhibit expression of the target gene, a method such as gene therapy is provided as an effective gene knock-down method.

In the present invention, types of siRNAs may be used without limitation as long as they can inhibit the expression of the PMP22 mutant gene. For example, the siRNA may preferably include a base sequence having a homology of 80%, preferably 90%, and more preferably 100% with respect to the base sequence of SEQ ID NO: 2, 3 or 4.

The siRNA of the present invention may be prepared using a method of preparing an RNA molecule known in the related art. For example, the siRNA may be prepared by a chemical synthetic method and an enzymatic method using RNA polymerase.

In the present invention, the term "small hairpin RNA" or "shRNA" refers to a nucleotide sequence which consists of 50 to 60 bases as a single strand and has a stem-loop structure in vivo. That is, the shRNA has an RNA sequence having a tight hairpin structure to inhibit gene expression through RNA interference. Long RNA consisting of 15 to 30 nucleotides form base pairs at both ends of a loop region consisting of 5 to 10 nucleotides to form a double-stranded stem. For expression to be manifested, the shRNA is transfected into cells using a vector containing a U6 promoter, and usually transferred to daughter cells so that the suppression of gene expression is inherited. The hairpin structure of the shRNA is cleaved by an intracellular mechanism to form siRNA, which then binds to RNA-induced silencing complexes (RISCs). Such RISCs bind to mRNA to cleave the mRNA. The shRNA is transcribed by RNA polymerase. According to the present invention, an shRNA structure consisting of a double-stranded stem sequence in which the nucleotide sequences of the present invention are present at both ends of the loop region may be constructed.

In the present invention, the term "aptamer" refers to a single-stranded DNA (ssDNA) or RNA having high specificity and affinity to a certain substance. Because the aptamer is stable and has very high affinity to the certain substance, the aptamer has been developed a lot, and widely applied to therapeutic agents and diagnostic sensors using the aptamer.

The present invention provides a recombinant vector including the siRNA, and the recombinant vector may be prepared using a recombinant DNA method known in the related art. In this case, the siRNA is preferably operably linked to a promoter so that the siRNA is suitably transcribed in cells to which the siRNA is transferred. The promoter may be used without limitation as long as the promoter is functional in eukaryotic cells. In this case, the promoter may also further include regulatory sequences including a leader sequence, a polyadenylation sequence, an enhancer, an upstream activation sequence, a signal peptide sequence, and a transcription termination factor, when necessary, for effective transcription.

In the present invention, the "siRNA delivery system" is preferably a non-viral delivery system. For example, the siRNA delivery system includes various plasmids and liposomes (i.e., lipid polymers) which may be expressed in eukaryotic cells.

In the present invention, the "pharmaceutical composition" may further include components such as conventional therapeutically active ingredients, other adjuvants, pharmaceutically acceptable carriers, etc. The pharmaceutically acceptable carriers include saline, sterile water, Ringer's solution, buffered saline, dextrose solutions, maltodextrin solutions, glycerol, and ethanol.

The composition may be formulated into oral preparations such as a powder, a granule, a tablet, a capsule, a suspension, an emulsion, syrup, an aerosol, etc., and forms of a liquid for external use, a suppository and a sterile injectable solution using conventional methods.

In the present invention, it is apparent to those skilled in the art that the "dose" may be widely adjusted depending on the weight, age, sex, health condition, and diet of a patient, an administration time, an administration mode, a secretion rate, and the severity of a disease.

In the present invention, the "subject" refers to a target in need of treatment of a disease, more particularly to a mammal such as a human or non-human primate, a mouse, a rat, a dog, a cat, a horse, and cattle.

In the present invention, a range of the "pharmaceutically effective amount" may be determined depending on the type and severity a disease in a patient, the age and sex of a patient, the sensitivity to the drug to be administered, an administration time, a route of administration, and a secretion rate, a therapeutic period, factors including drugs to be used in combination, and other factors well known in the field of medicine. In this case, the pharmaceutically effective amount may be easily determined by those skilled in the related art as an amount sufficient to obtain the maximum effect without any side effects in consideration of all the factors.

The "administration method" may be used without limitation as long as the composition of the present invention can reach a target tissue. For example, the administration method includes oral administration, intra-arterial injection, intravenous injection, percutaneous injection, intranasal administration, transbronchial administration, or intramuscular administration. The daily dose is in a range of approximately 0.0001 to 100 mg/kg, preferably in a range of 0.001 to 10 mg/kg. In this case, the composition may be administered once a day or multiple times in divided doses.

In the present invention, 19 allele-specific siRNAs are designed and a luciferase assay is then performed in vitro on Trembler J (Tr-J) mice in which a mutation (Leu16Pro) naturally occurs in Pmp22 in order to determine whether the siRNA specifically and selectively reduces an expression level of the mutant allele and inhibits a decline in viability of Schwann cells caused by overexpression of mutant Pmp22. Also, the in vivo efficacy of the allele-specific siRNA is assessed by intraperitoneally injecting the siRNA into Tr-J mice.

As a result, it is confirmed that the motor function of the mice is improved and a volume of muscle is increased when the allele-specific siRNA is administered into the mice, as assessed through a rotarod test and magnetic resonance image analysis, respectively. Also, it is confirmed that a motor nerve conduction velocity and a compound muscle action potential are improved.

Also, it is confirmed that myelination in sciatic nerves of the mice is remarkably increased after the siRNA is administered, as observed through Toluidine Blue staining and electron microscopy. Also, the suppression of expression of Pmp22 mutant allele mRNA in Schwann cells of the Tr-J mice is validated, and an increase in expression levels of myelinating proteins as myelin basic protein (Mbp) and myelin protein zero (Mpz) is observed. The sciatic nerves of the Tr-J mice exhibits demyelinating characteristics from early stages after birth, but a demyelinating phenomenon is clearly improved through administration of the allele-specific siRNA according to the present invention, the number of myelinated nerve fibers increases, and a thickness of myelin is improved. Such structural improvements are positively associated with a significant increase in electrophysiological parameters such as MNCV and CMAP.

Further, to assess the clinical usefulness of the target gene-specific siRNA, a non-viral delivery strategy is applied in the present invention. Although the delivery of shRNA using viruses is effective for long-term suppression of gene expression, current clinical applications are limited. On the other hand, various clinical trials have been conducted using siRNA for treating diseases, which targets a detrimental protein using a lipid polymer as a vehicle. The present inventors have also used a commercially available lipid polymer for in vivo delivery of the allele-specific siRNA.

Although there have been no reports regarding the efficacy of lipid polymers on in vivo delivery of nucleotides for targeting Schwann cells, it was first observed that an expression level of the target gene in the Schwann cells is reduced, indicating that the allele-specific siRNA is successfully delivered. Therefore, the results of the present invention demonstrate that the lipid polymer is available as a vehicle for targeting the Schwann cells.

In the present invention, to address the clinical applicability of the allele-specific siRNA, 19 allele-specific siRNAs targeting the same mutations as the human PMP22 were designed, and two siRNAs (hTr12 and hTr15) having an ability to selectively suppress expression of the PMP22 mutant allele were finally isolated.

The results suggest that the selective suppression of the PMP22 mutant allele via the non-viral delivery of the siRNA improves demyelinating neuropathy symptoms of CMT in vivo, indicating that the allele-specific siRNA may be effective for a therapeutic strategy with respect to peripheral neuropathy which is dominantly inherited.

Hereinafter, preferred embodiments are provided to aid in understanding the present invention. However, it should be understood that detailed description provided herein is merely intended to provide a better understanding of the present invention, and is not intended to limit the scope of the present invention.

EXAMPLES

Example 1

Experimental Method 1-1. Preparation of Pmp22 Constructs

To obtain the Pmp22 gene, total mRNA from NIH3T3 mouse fibroblast cells was used as a template for cDNA synthesis and PCR amplification. The amplified gene was cloned into a psiCheck2 vector (Promega, Madison, Wis., USA) harboring hRluc and hluc genes.

To evaluate the efficiency of siRNA, the Pmp22 gene was cloned at a 3' flanking region of hRluc. To generate the L16P mutation, site-directed mutagenesis was induced using a QuikChange site-directed mutagenesis kit (Stratagene, La Jolla, Calif., USA). A pair of primers for mutagenesis was as follows. Here, all the sequences were confirmed through capillary sequencing.

```
Pmp22-L16P Forward Primer:
5'-ATCGCGGTGCCAGTGTTGCTCTTCGT-3'    (SEQ ID NO: 5)

Pmp22-L16P Reverse Primer:
5'-GAGCAACACTGGCACCGCGATGTGCA-3'    (SEQ ID NO: 6)
```

1-2. Design and Selection of Allele-Specific siRNA

Allele-specific siRNAs and a control-siRNA were synthesized at Bioneer Inc. (Daejeon, Korea). Transfection of siRNAs or DNA vectors was performed using a Lipofectamine 3000 reagent (Invitrogen, Carlsbad, Calif., USA).

The allele-specificity of siRNAs was determined by comparing the activities of renilla and firefly luciferases using a dual luciferase assay kit (Promega) after human embryonic kidney cells (HEK 293T) were transfected with either a wild-type gene- or L16P Pmp22-containing vector in combination with a varying concentration of siRNA. The Pmp22 gene was also cloned into an expression vector pCMV-myc (Clontech, Mountain View, Calif., USA).

1-3. Cell Culture and Analysis of Cells Viability

HEK 293T cells and rat Schwann cells (RT4) were cultured in Dulbecco's modified Eagle's media (DMEM; Biowest, Nuaille, France) supplemented with 10% fetal bovine serum (FBS) and 1% penicillin/streptomycin. The viability of the RT4 cells was determined after the RT4 cells were transfected with a wild-type gene or an L16P Pmp22 gene. The RT4 cells were seeded on 24-well plates at a density of $4 \times 10^4$ cells/well, and were transfected with the Pmp22-overexpressing vector and siRNA for 72 hours. Thereafter, the cell viability was determined using a 3-(4,5-dimethylthiazol-2-yl)-2,5-diphenyltetrazolium bromide (MTT) assay. The relative number of viable cells was determined by measuring the absorbance at 560 nm.

1-4. In vivo Delivery of siRNAs

All experiments on animals were performed according to the protocols approved by the Institutional Animal Care and Use Committees of Samsung Medical Center. Genotyping of the Tr-J mice was performed by direct sequencing of the Pmp22 gene.

Administration of siRNAs was performed from postnatal day 6, and a mixed solution of siRNA (750 pmole/mouse) and 2 μl of Avalanche-in vivo transfection reagent (EZ Biosystems, College Park, Md., USA) was intraperitoneally administered a total of five times at intervals of 3 days.

1-5. Rotarod Test

To evaluate motor coordination and balance of the mice, a rotarod test was performed on a 3-cm-long horizontal rotating rod (2 m/min). To adapt the mice to this test, the mice were pre-trained for 3 days, and the test was performed for up to 5 minutes.

1-6. Electrophysiological Study

For electrophysiological evaluation, a nerve conduction study (NCS) was performed. More specifically, mice were anesthetized with $CO_2$ gas, and maintained in an anesthetized state with supply of 1.5% isoflurane using a nose cone during this experiment. The NCS was performed using a Nicolet VikingQuest device (Natus Medical, San Carlos, Calif., USA).

1-7. Toluidine Staining and Electron Microscopy

Sciatic nerves were biopsied from the mice, and lesions were observed using optical and electron microscopes. Each of the specimens was fixed in 2% glutaraldehyde diluted with a 25 mM cacodylate buffer, and semi-thin sections were stained with Toluidine Blue. Thereafter, the ultra-thin cut samples were counterstained with uranyl acetate and lead citrate. The samples were incubated for an hour in 1% $OsO_4$, sequentially dehydrated in ethanol, passed through propylene oxide, and the embedded in an epoxy resin (Epok 812, 02-1001; Oken, Nagano, Japan). The ultra-thin sections having a thickness of 60 nm were collected on a 200-mesh nickel grid, and stained with 1% uranyl acetate and Reynolds' lead citrate for 10 minutes. Then, the samples were observed using a HT7700 electron microscope (Hitachi, Tokyo, Japan) at 80 kV.

1-8. Quantitation of mRNA

An RNeasy Plus Mini kit (Qiagen, Hilden, Germany) was used to quantify an expression level of mRNA, and total mRNA was prepared to perform quantitative RT-PCR. Thereafter, cDNA was synthesized from 2 μg of the total mRNA using SuperScript™ II reverse transcriptase (Invitrogen). Then, 2 μL of the synthesized cDNA was prepared, and PCR amplification was performed using the cDNA as a template and pairs of primers below.

Pmp22 Forward Primer:
5'-ATGGACACACGACTGATCTCT-3'        (SEQ ID NO: 7)

Pmp22 Reverse Primer:
5'-CAGCCATTCGCTCACTGATGA-3'        (SEQ ID NO: 8)

Mbp Forward Primer:
5'-GACCATCCAAGAAGACCCCAC-3'        (SEQ ID NO: 9)

(Tr-J) mice were used as a model system. The mice harbored a naturally occurring Leu16Pro mutation in the Pmp22 gene, and the mutation is found in human CMT patients.

First, 19 different types of siRNAs (mTr1 to mTr19) specifically targeting an L16P mutant (c.47T>C) (SEQ ID NO:16) were designed based on a Pmp22 (NCBI Accession No. NM_001302255.1) sequence (SEQ ID NO:15) of the Tr-J mouse, and base sequences of such siRNAs are as listed in the following Table 1.

TABLE 1

| | | |
|---|---|---|
| Pmp22-WT | | 5'-CTGTTCCTGCACATCGCGGTGCTAGTGTTGCTCTTCGTCTCCACCATCG-3' |
| Pmp22-L16P | | 5'-CTGTTCCTGCACATCGCGGTGCCAGTGTTGCTCTTCGTCTCCACCATCG-3' |
| mTr1 | | 5'-UCCUGCACAUCGCGGUGCCdTdT-3' (SEQ ID NO: 17) |
| mTr2 | | 5'-CCUGCACAUCGCGGUGCCAdTdT-3' (SEQ ID NO: 18) |
| mTr3 | | 5'-CUGCACAUCGCGGUGCCAGdTdT-3' (SEQ ID NO: 19) |
| mTr4 | | 5'-UGCACAUCGCGGUGCCAGUdTdT-3' (SEQ ID NO: 20) |
| mTr5 | | 5'-GCACAUCGCGGUGCCAGUGdTdT-3' (SEQ ID NO: 21) |
| mTr6 | | 5'-CACACGCGGUGCCAGUGUdTdT-3' (SEQ ID NO: 22) |
| mTr7 | | 5'-ACAUCGCGGUGCCAGUGUUdTdT-3' (SEQ ID NO: 23) |
| mTr8 | | 5'-CAUCGCGGUGCCAGUGUUGdTdT-3' (SEQ ID NO: 24) |
| mTr9 | | 5'-AUCGCGGUGCCAGUGUUGCdTdT-3' (SEQ ID NO: 25) |
| mTr10 | | 5'-UCGCGGUGCCAGUGUUGCUdTdT-3' (SEQ ID NO: 26) |
| mTr11 | (SEQ ID NO: 27) | 5'-CGCGGUGCCAGUGUUGCUCdTdT-3' |
| mTr12 | (SEQ ID NO: 28) | 5'-GCGGUGCCAGUGUUGCUCUdTdT-3' |
| mTr13 | (SEQ ID NO: 29) | 5'-CGGUGCCAGUGUUGCUCUUdTdT-3' |
| mTr14 | (SEQ ID NO: 30) | 5'-GGUGCCAGUGUUGCUCUUCdTdT-3' |
| mTr15 | (SEQ ID NO: 31) | 5'-GUGCCAGUGUUGCUCUUCGdTdT-3' |
| mTr16 | (SEQ ID NO: 32) | 5'-UGCCAGUGUUGCUCUUCGUdTdT-3' |
| mTr17 | (SEQ ID NO: 33) | 5'-GCCAGUGUUGCUCUUCGUCdTdT-3' |
| mTr18 | (SEQ ID NO: 34) | 5'-CCAGUGUUGCUCUUCGUCUdTdT-3' |
| mTr19 | (SEQ ID NO: 35) | 5'-CAGUGUUGCUCUUCGUCUCdTdT-3' |

-continued

Mbp Reverse Primer:
5'-GCCATAATGGGTAGTTCTCGTGT-3'      (SEQ ID NO: 10)

Mpz Forward Primer:
5'-CGGACAGGGAAATCTATGGTGC-3'       (SEQ ID NO: 11)

Mpz Reverse Primer:
5'-GCGCCAGGTAAAAGAGATGTCA-3'       (SEQ ID NO: 12)

Actin Forward Primer:
5'-GTGACGTTGACATCCGTAAAGA-3'       (SEQ ID NO: 13)

Actin Reverse Primer:
5'-GCCGGACTCATCGTACTCC-3'          (SEQ ID NO: 14)

1-9. Western Blotting

Western blotting was performed using either RT4 cells or mouse sciatic nerves. Anti-BiP, anti-p62 (Cell Signaling Technology, Beverly, Mass., USA), anti-PMP22 (Novus Biologicals, Littleton, Colo., USA), anti-MBP, anti-MPZ, anti-myc (Abcam, Cambridge, UK), and anti-β-actin (Sigma-Aldrich, St. Louis, Mo., USA) antibodies were used as primary antibodies to determine expression levels of the proteins.

1-10. Statistical Analysis

All animals were used for studies using a blind test. The comparison between experimental groups was made using a Student's t-test. A value of $P<0.05$ was considered to be statistically significant.

Example 2

Experimental Results 2-1. Isolation of siRNAs Specific to Mouse Pmp22-L16P Allele To check whether target gene-specific siRNA may alleviate the pathophysiologic symptoms of CMT, Trembler-J To evaluate each of the designed siRNAs, a dual luciferase vector in which a hRluc gene was flanked by either a wild-type or L16P mutant Pmp22 gene was constructed, and HEK 293T cells were then transfected with the vector. After treatment with the siRNA, the ratio of luciferase activity between Rluc regulated by a 5'-flanking Pmp22 gene and hluc independent from a Pmp22 gene was measured.

As a result, it was confirmed that the control-siRNA had no influence on either the wild-type Pmp22 gene (WT) or the L16P mutant Pmp22 gene, as shown in FIG. 1. Although most of the siRNAs targeting Pmp22-L16P did not show allele-specificity, it was revealed that mTr3 and mTr11 selectively suppressed the L16P mutant Pmp22 gene by 29.6% and 30.7%, respectively, when present at a concentration of 5 nM. Further, it was revealed that the specificity of the siRNA to the mutant allele was clearly observed at a concentration of 100 nM.

After the siRNAs (mTr3 and mTr11) specific to the mutant allele were screened in vitro, HEK 293T cells overexpressing either the wild-type Pmp22 gene or the L16P mutant Pmp22 gene were treated with the siRNAs to perform real-time PCR.

Figure 2:
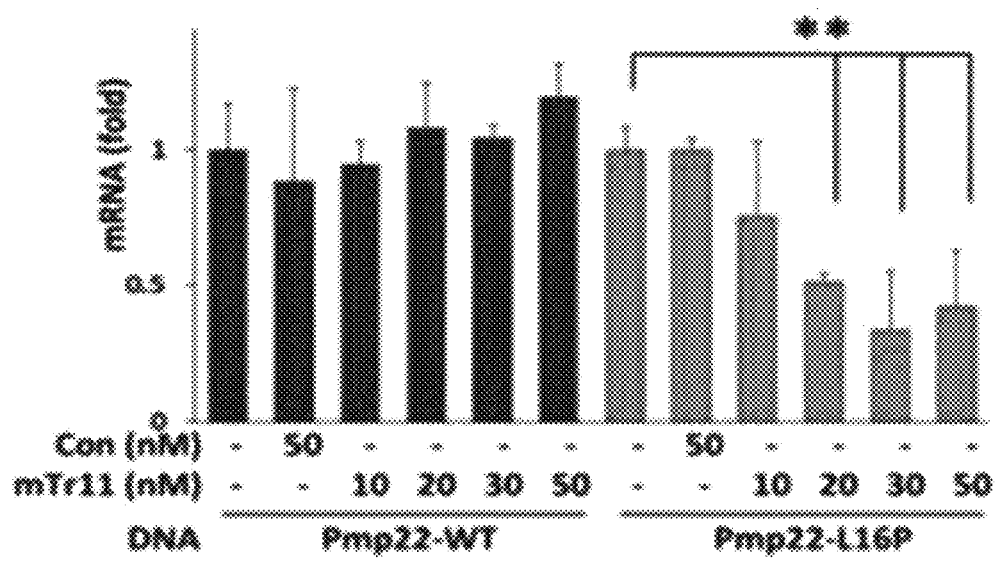
FIG. 2 shows results obtained by treating HEK 293T cells, which overexpress a wild-type Pmp22 gene or an L16P mutant Pmp22 gene, with siRNA (mTr11) specific to a Pmp22-L16P mutant gene and subjecting to real-time polymerase chain reaction (PCR)
Figure 3:
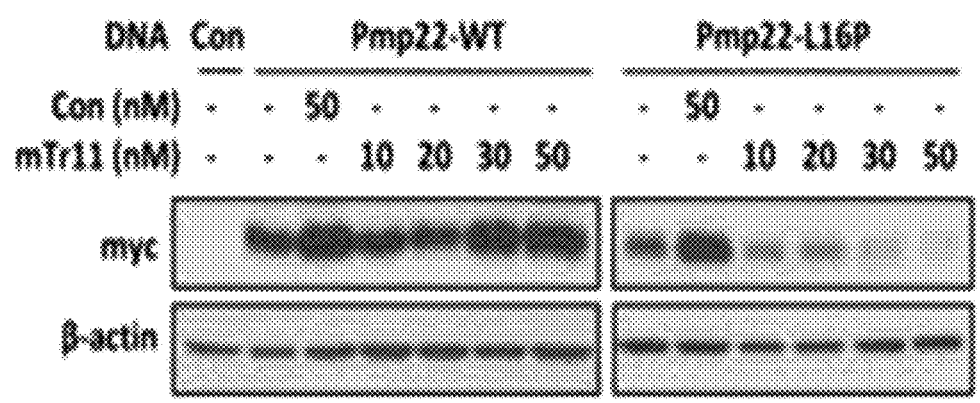
FIG. 3 shows results obtained by treating HEK 293T cells, which overexpress a wild-type Pmp22 gene or an L16P mutant Pmp22 gene, with siRNA (mTr11) specific to the Pmp22-L16P mutant gene and subjecting to Western blotting.

As a result, it was confirmed that an mRNA expression level of the L16P mutant Pmp22 gene was proportionally suppressed in a concentration-dependent manner when the HEK 293T cells were treated with mTr11 (siRNA having a sequence set forth in SEQ ID NO: 2), as shown in FIG. 2, and that a protein expression level of the L16P mutant Pmp22 gene also decreased when the HEK 293T cells were transfected with mTr11, as shown in FIG. 3.

Figure 4:
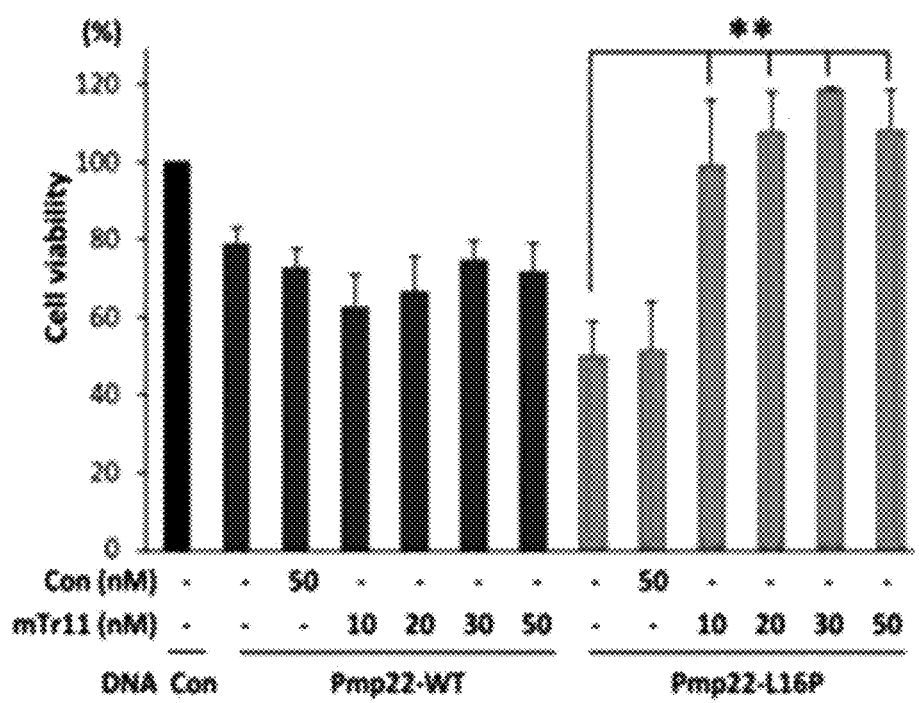
FIG. 4 shows results obtained by treating RT4 cells, which overexpress a wild-type Pmp22 gene or an L16P mutant Pmp22 gene, with siRNA (mTr11) specific to the Pmp22-L16P mutant gene and subjecting to an MTT assay.

Further, after either a wild-type Pmp22 gene or a mutant Pmp22 gene was overexpressed in RT4 cells to induce cell death, it was investigated whether the cell death was inhibited by suppressing Pmp22 expression when the cells were treated with mTr11. As a result, it was confirmed that the viability of the RT4 cells overexpressing the Pmp22-L16P remarkably increased due to the treatment with mTr11, as shown in FIG. 4. These results indicated that mTr11 exhibited high specificity to the Pmp22-L16P allele.

2-2. Improvement of Motor Function by Pmp22-L16P Allele-Specific siRNA

Figure 5:
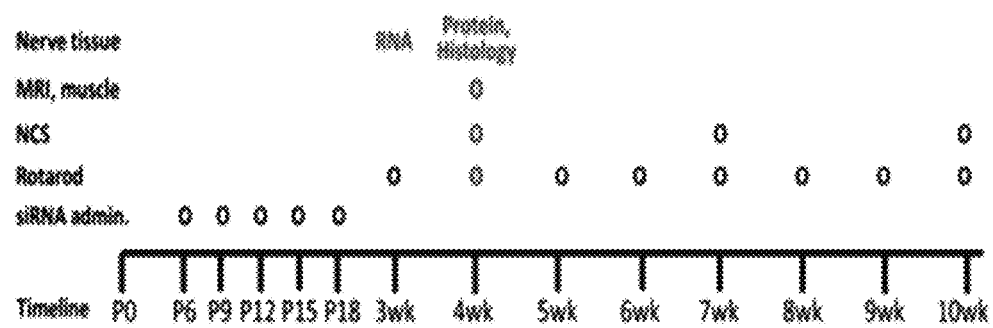
FIG. 5 is a schematic diagram of an experimental model for evaluating whether siRNA (mTr11) specific to the Pmp22-L16P mutant gene improve an abnormal neuropathic phenotype of CMT using Tr-J mice.

The Tr-J mice were used to evaluate whether the target gene-specific siRNA (mTr11) selected in Example 2-1 ameliorated the abnormal neuropathic phenotypes of CMT. The control-siRNA or mTr11 was intraperitoneally administered into the mice showing peripheral neuropathic symptoms until 3 weeks after birth for a total of 5 times at intervals of 3 days from postnatal day 6 (P6) (see FIG. 5).

Figure 6:
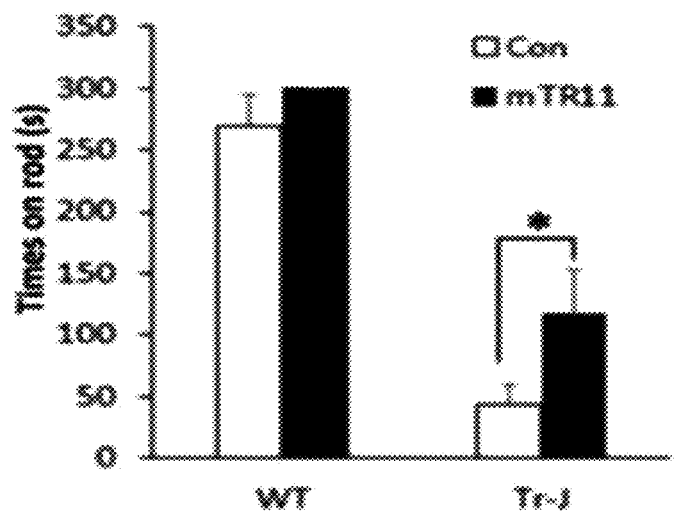
FIG. 6 shows results obtained by performing a rotarod test after siRNA (mTr11) specific to the Pmp22-L16P mutant gene is administered into the Tr-J mice.

After the last administration of the siRNAs, a rotarod test was performed. As a result, it was observed that the rotarod performance was improved in the Tr-J mice to which the mTr11 was administered, as shown in FIG. 6.

Figure 7:
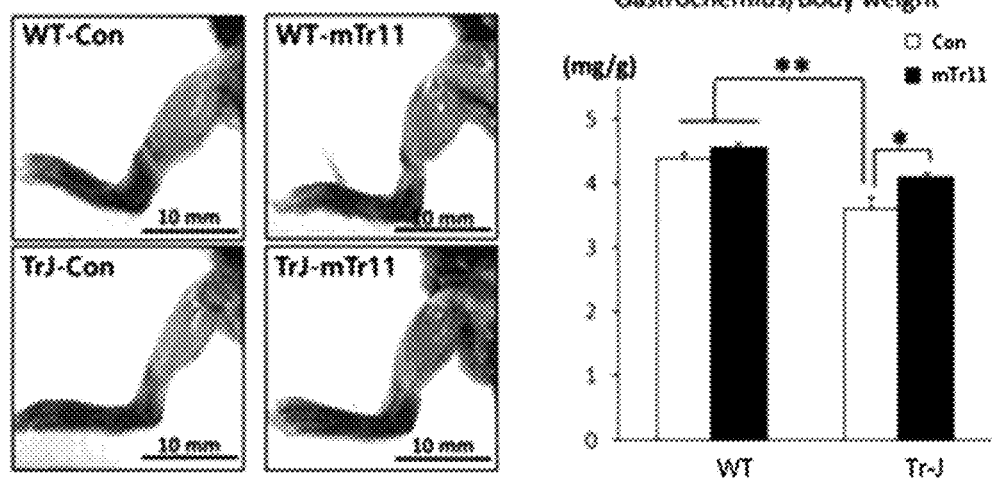
FIG. 7 shows results of determining a change in volume of muscle after siRNA (mTr11) specific to the Pmp22-L16P mutant gene is administered to the Tr-J mice.

To check whether a volume of muscle was changed in the Tr-J mice to which the mTr11 was administered, an amount of gastrocnemius muscle in each group was also measured. As a result, as shown in FIG. 7, it was revealed that there was no difference in volume of muscle between the groups of wild-type mice treated with the control and the mTr11 siRNA. On the other hand, it was revealed that, when mTr11 was administered into the Tr-J mice, the volume of muscle of the Tr-J mice increased by 10% compared to when the control-siRNA was administered into the Tr-J mice, a value which is equivalent to 80% of the muscle volume of the wild-type mice.

Next, because the atrophy of lower limb muscle in CMT patients was due to fat infiltration, the mice were subjected to magnetic resonance imaging (MRI). In this case, the in vivo monitoring was performed using the Biospec 7.0 Tesla 30 cm horizontal bore scanner with Paravision 5.1 software (Bruker Biospin MRI GmbH, Germany).

Based on the T1 image results, it was confirmed that the hind limb muscle was remarkably reduced in the Tr-J mice to which the control-siRNA was administered, compared to the wild-type mice. On the other hand, it was confirmed that a cross-sectional area of the hind limb muscle in the Tr-J mice was significantly increased in the Tr-J mice to which mTr11 was administered.

Therefore, it can be seen that, when the siRNAs having specific sequences according to the present invention were used, the siRNAs were effective in increasing an anatomical muscle volume as well as improving the motor function in vivo.

2-3. Effect of Pmp22-L16P Allele-Specific siRNA on Neurophysiological Improvement To check whether the enhancement of motor function after the mTr11 administration was due to the structural and functional improvement of peripheral nerves, nerve electrophysiology was evaluated.

Figure 8:
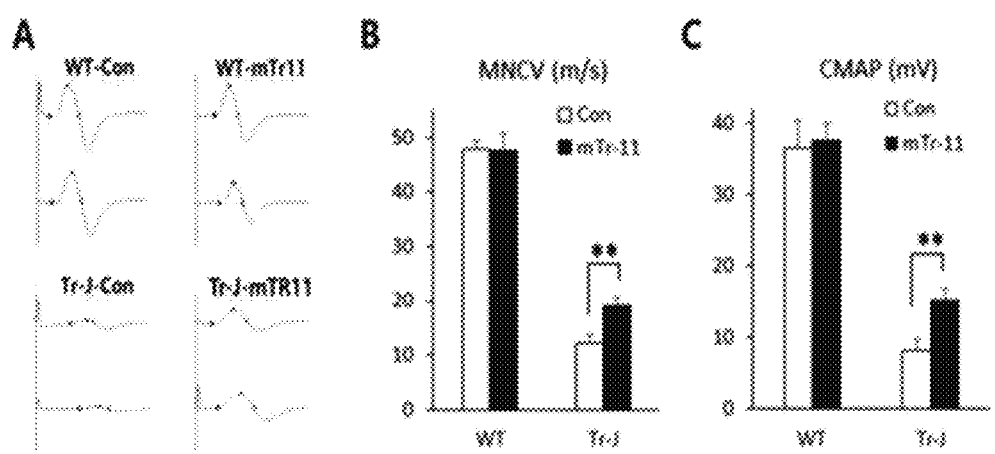
FIG. 8 shows results of determining an effect on nerve electrophysiological improvement after siRNA (mTr11) specific to the Pmp22-L16P mutant gene is administered to the Tr-J mice, particularly distal latency (FIG. 8A), motor nerve conduction velocity (FIG. 8B), and compound muscle action potential (FIG. 8C)

As a result, as shown in FIGS. 8A, 8B and 8C, it was revealed that the Tr-J mice exhibited delayed distal latency (DL), slow motor nerve conduction velocity (MNCV), and reduced compound muscle action potential (CMAP), compared to the wild-type mice. On the other hand, it was revealed that the Tr-J mice to which mTr11 was administered exhibited remarkably improved MNCV and CMAP, compared to the Tr-J mice to which the control-siRNA was administered.

Next, to histologically assess the integrity of peripheral nerves using tissue sections of sciatic nerves, Toluidine Blue staining was performed.

Figure 9:
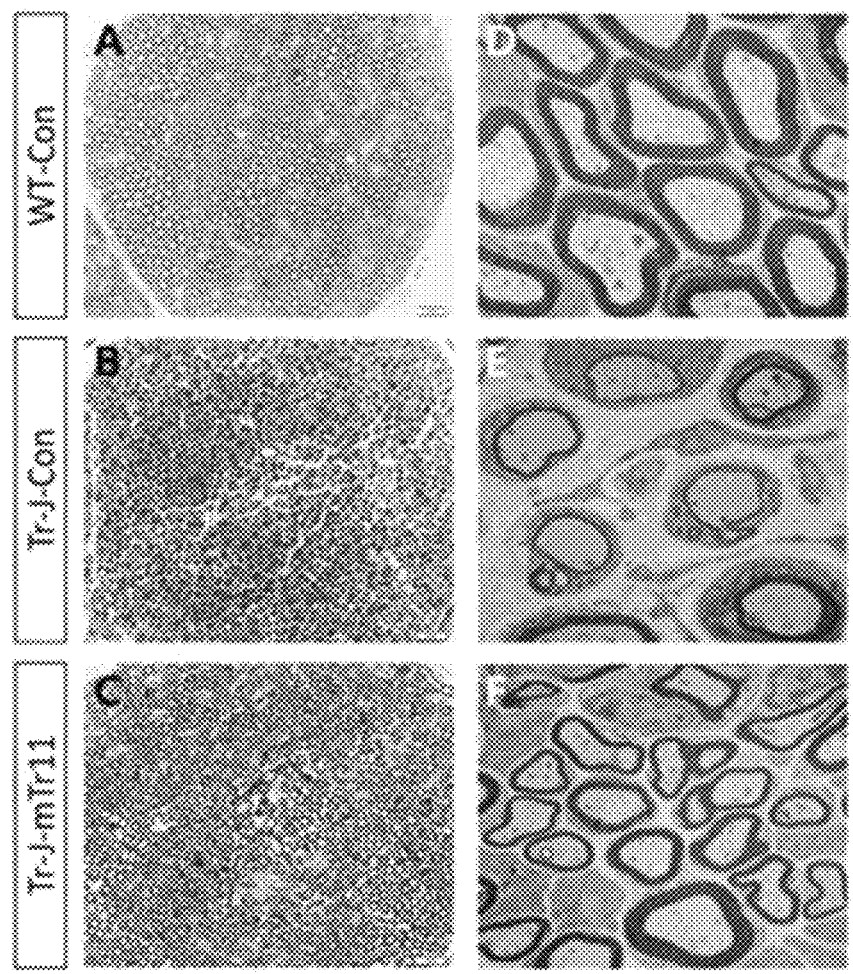
FIG. 9 shows results obtained by subjecting nervous tissue sections to Toluidine Blue staining and electron microscopy after siRNA (mTr11) specific to the Pmp22-L16P mutant gene is administered to the Tr-J mice.

As a result, as shown in FIGS. 9A, 9B and 9C, it was revealed that the number of demyelinating or dysmyelinating Schwann cells in the sciatic nerves increased in the case of the Tr-J mice to which mTr11 was administered, compared to the wild-type mice. On the other hand, it was revealed that a myelination pattern in the sciatic nerves was enhanced in the case of the Tr-J mice to which the mTr11 was administered.

Also, as shown in FIGS. 9D, 9E and 9F, it was revealed that the myelination pattern in the axons compared was enhanced in the case of the Tr-J mice to which mTr11 was administered, compared to the Tr-J mice to which the control-siRNA was administered, as observed in the electron microscopic images of the sciatic nerves.

Figure 10:
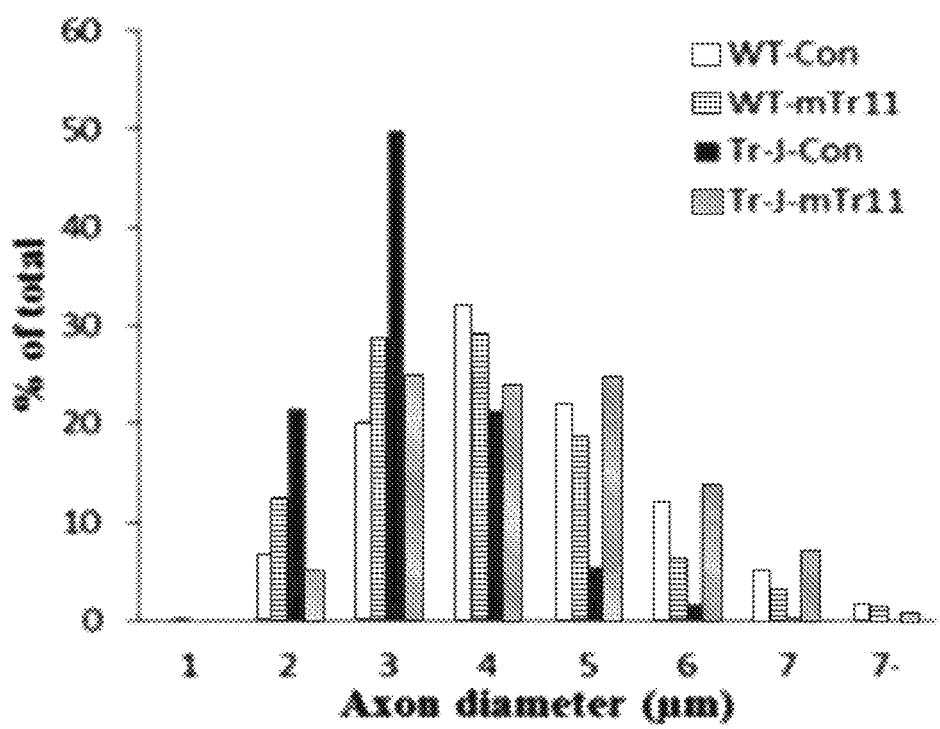
FIG. 10 shows results obtained by measuring diameters of myelinated nerve fibers and axons to quantitatively analyze Toluidine Blue staining.

In addition, to quantitatively analyze the Toluidine Blue staining images, the diameters of myelinated nerve fibers and axons were measured. Then, the pattern of axonal diameter distribution was measured. As a result, as shown in FIG. 10, it was revealed that a decrease in large myelinated nerve fibers in the Tr-J mice was observed, which was typical for CMT1 patients. On the other hand, it was revealed that no patterns significantly different from that of the wild-type mice were observed in the Tr-J mice to which mTr11 was administered.

Figure 11:
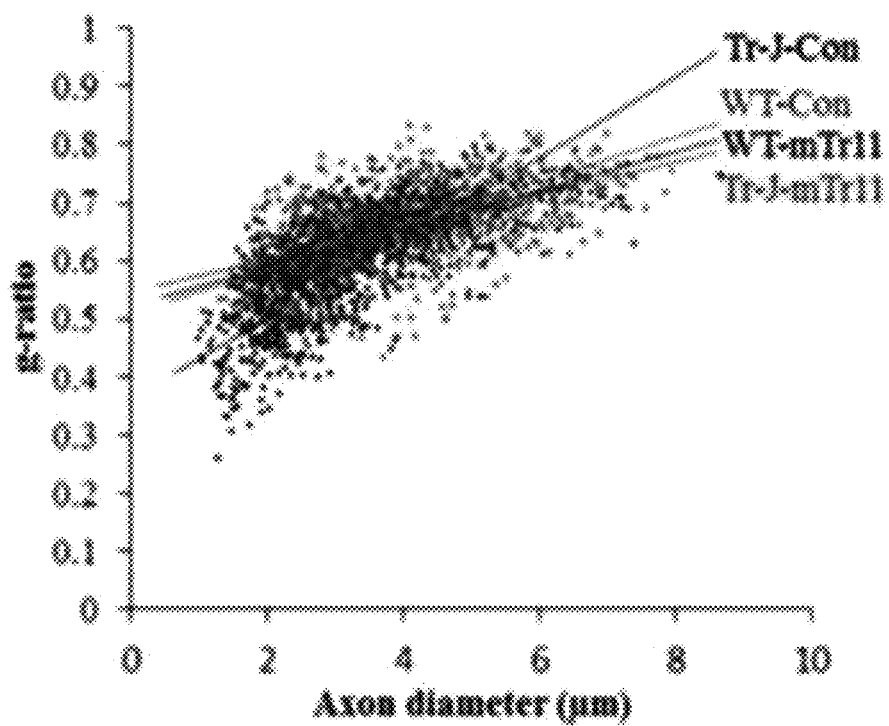
FIG. 11 shows results obtained by measuring g-ratios after siRNA (mTr11) specific to the Pmp22-L16P mutant gene is administered to Tr-J mice.

Also, as shown in FIG. 11, it was revealed that the g-ratio of the Tr-J mice to which mTr11 was administered showed a decline in abnormal myelination, whereas the Tr-J mice to which the control-siRNA was administered had a sharper slope than the wild-type mice.

The results showed that the administration of mTr11 remarkably improved myelination of the sciatic nerves in the Tr-J mice.

2-4. Allele-Specific Decrease of Mutant Pmp22 in vivo

In the above Examples, it was confirmed that the siRNA (mTr11) of the present invention specific to the Pmp22-L16P mutant gene had anatomical, physiological, and behavioral improvement effects in the Tr-J mice when the siRNA (mTr11) was administered to the Tr-J mice. Therefore, an mRNA expression level of each of the wild-type Pmp22 gene and the L16P mutant Pmp22 allele in the Tr-J mice was measured after mTr11 administration in order to validate whether such improvement effects were achieved by suppressing the expression of the mutant Pmp22 allele.

Figure 12:
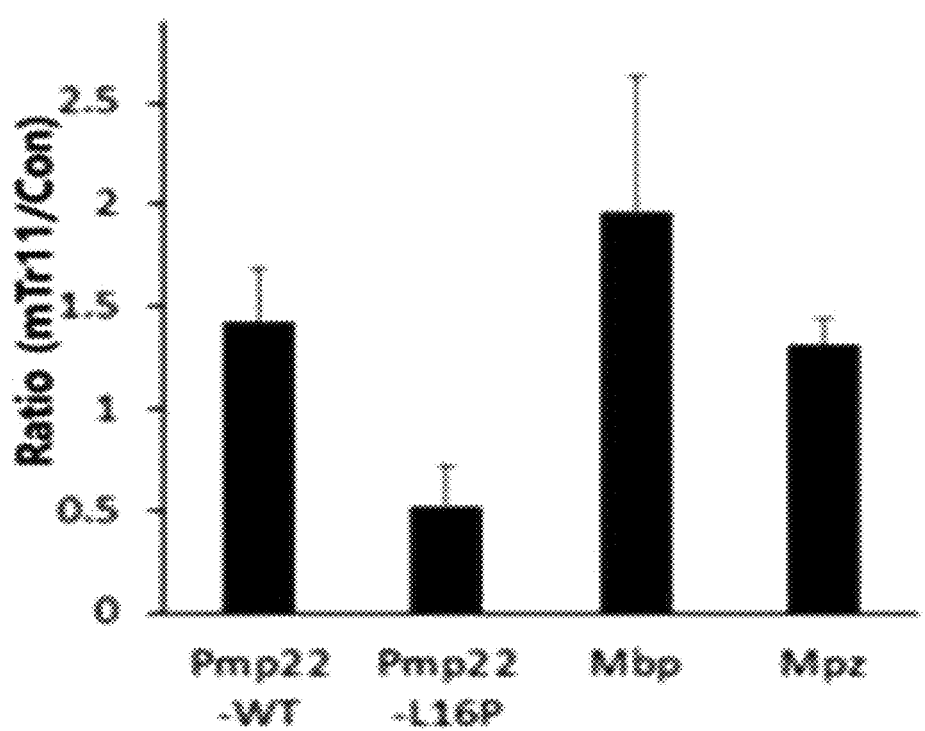
FIG. 12 shows results of measuring and quantifying respective mRNA expression levels of a wild-type Pmp22 gene, an L16P mutant Pmp22 allele, Mbp, and Mpz in sciatic nerves after siRNA (mTr11) specific to the Pmp22-L16P mutant gene is administered to Tr-J mice.

To quantify each of the alleles, allele-specific amplification was performed using allele-specific primers. The expression levels of the wild-type gene and the Pmp22-L16P allele in the sciatic nerves of the Tr-J mice to which mTr11 was administered were compared using the above method As a result, as shown in FIG. 12, the mRNA expression level of the L16P allele in the Tr-J mice to which mTr11 was administered decreased by 51%, and the mRNA expression level of the wild-type allele increased 1.4-fold, compared to the Tr-J mice to which the control-siRNA was administered.

Figure 13:
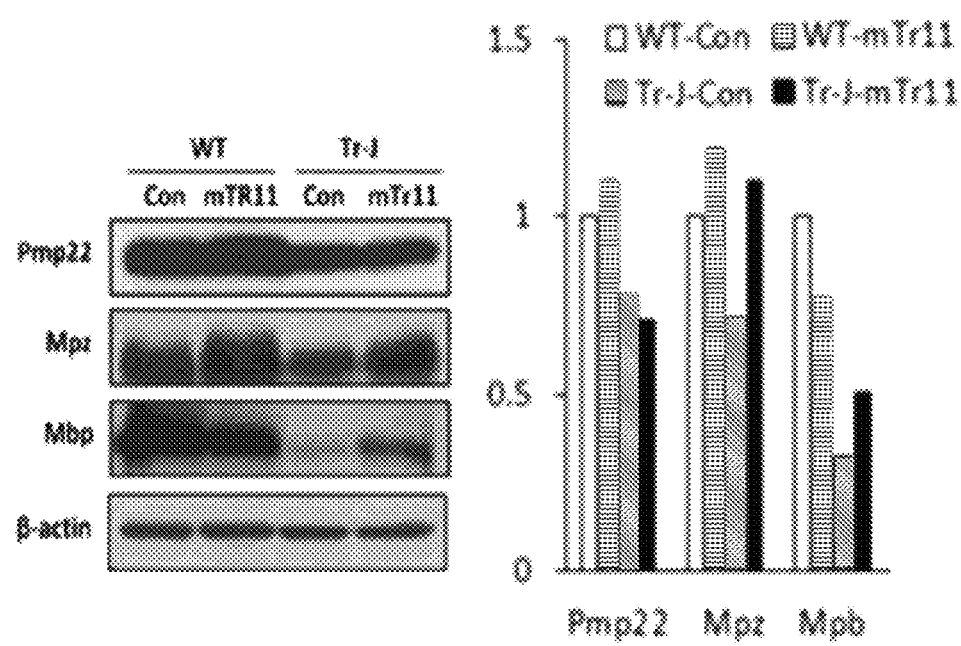
FIG. 13 shows results obtained by performing Western blotting to observe expression levels of Mbp and Mpz proteins in the sciatic nerves after siRNA (mTr11) specific to the Pmp22-L16P mutant gene is administered to Tr-J mice.

Also, as shown in FIG. 13, it was confirmed that the protein expression levels of the other myelin protein genes Mbp and Mpz increased in the sciatic nerves of the mice to which mTr11 was administered. Because the expression of such proteins is decreased in the Tr-J mice compared to the wild-type mice, the results suggested that the increased expression of Mbp and Mpz due to the mTr11 administration correlated with enhanced myelination of the Schwann cells. The expression level of the Pmp22 did not increase in the mice to which mTr11 was administered because the sum of mRNA of the mutant allele whose expression was suppressed by the mTr11 administration and mRNA of the wild-type gene increased.

In addition, the expression of markers for endoplasmic reticulum stress (BiP) and autophagy (p62) increased in the Tr-J mice as known in the art. This was because an increase in expression of the markers was known to be due to a cytotoxic effect of the mutant Pmp22 protein. Therefore, an effect of mTr11 on the expression of the BiP and p62 markers was examined.

Figure 14:
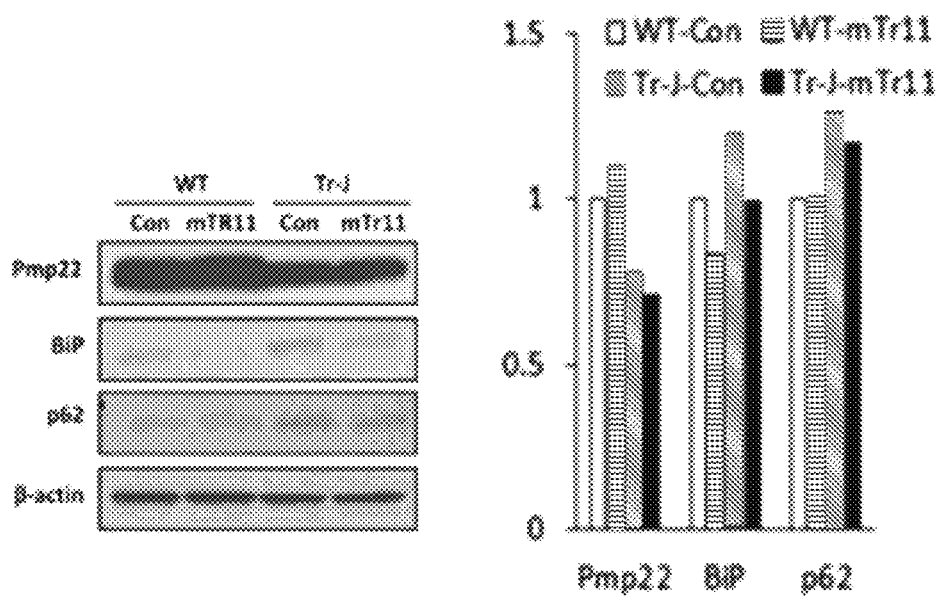
FIG. 14 shows results obtained by performing Western blotting to observe expression levels of BiP and p62 proteins in the sciatic nerves after siRNA (mTr11) specific to the Pmp22-L16P mutant gene is administered to Tr-J mice.

As a result, as shown in FIG. 14, it can be seen that the expression levels of the BiP and p62 proteins were reduced by the mTr11 administration. Based on these results, it can be seen that the cytotoxic effect of partially abnormal Schwann cells was reduced as the expression level of the mutant allele Pmp22 protein was reduced by the mTr11 administration.

As described above, it was confirmed that the administration of the Pmp22 mutant allele-specific siRNA of the present invention was able to ameliorate various phenotypic symptoms of the Tr-J mice, and thus the siRNA of the present invention was able to be used in therapeutic methods useful for treating CMT disease.

2-5. Screening of siRNAs Specific to Human PMP22-L16P Allele

Nineteen siRNAs (hTr1 to hTr19) specifically targeting the L16P mutant (c.47T>C) (SEQ ID NO:37) were designed based on the human PMP22 (NCBI Accession No. NM_000304.2) sequence (SEQ ID NO:36), and the base sequences of such siRNAs are as listed in the following Table 2.

TABLE 2

| | |
|---|---|
| hPMP22-WT | 5'-CATCGTCCTCCACGTCGCGGTGCTGGTGCTGCTGTTCGTCTCCACGATC-3' |
| hPMP22-L16P | 5'-CATCGTCCTCCACGTCGCGGTGCCGGTGCTGCTGTTCGTCTCCACGATC-3' |
| hTr1 | 5'-UCCUCCACGUCGCGGUGCCdTdT-3' (SEQ ID NO: 38) |
| hTr2 | 5'-CCUCCACGUCGCGGUGCCGdTdT-3' (SEQ ID NO: 39) |
| hTr3 | 5'-CUCCACGUCGCGGUGCCGGdTdT-3' (SEQ ID NO: 40) |
| hTr4 | 5'-UCCACGUCGCGGUGCCGGUdTdT-3' (SEQ ID NO: 41) |
| hTr5 | 5'-CCACGUCGCGGUGCCGGUGdTdT-3' (SEQ ID NO: 42) |
| hTr6 | 5'-CACGUCGCGGUGCCGGUGCdTdT-3' (SEQ ID NO: 43) |
| hTr7 | 5'-ACGUCGCGGUGCCGGUGCUdTdT-3' (SEQ ID NO: 44) |
| hTr8 | 5'-CGUCGCGGUGCCGGUGCUGdTdT-3' (SEQ ID NO: 45) |
| hTr9 (SEQ ID NO: 46) | 5'-GUCGCGGUGCCGGUGCUGCdTdT-3' |
| hTr10 (SEQ ID NO: 47) | 5'-UCGCGGUGCCGGUGCUGCUdTdT-3' |
| hTr11 (SEQ ID NO: 48) | 5'-CGCGGUGCCGGUGCUGCUGdTdT-3' |
| hTr12 (SEQ ID NO: 49) | 5'-GCGGUGCCGGUGCUGCUGUdTdT-3' |
| hTr13 (SEQ ID NO: 50) | 5'-CGGUGCCGGUGCUGCUGUUdTdT-3' |
| hTr14 (SEQ ID NO: 51) | 5'-GGUGCCGGUGCUGCUGUUCdTdT-3' |
| hTr15 (SEQ ID NO: 52) | 5'-GUGCCGGUGCUGCUGUUCGdTdT-3' |
| hTr16 (SEQ ID NO: 53) | 5'-UGCCGGUGCUGCUGUUCGUdTdT-3' |
| hTr17 (SEQ ID NO: 54) | 5'-GCCGGUGCUGCUGUUCGUCdTdT-3' |
| hTr18 (SEQ ID NO: 55) | 5'-CCGGUGCUGCUGUUCGUCUdTdT-3' |
| hTr19 (SEQ ID NO: 56) | 5'-CGGUGCUGCUGUUCGUCUCdTdT-3' |

To evaluate each of the designed siRNAs, a dual luciferase vector in which a hRluc gene was flanked by either a wild-type or L16P mutant Pmp22 gene was constructed, and HEK 293T cells were then transfected with the vector. After treatment with the siRNA, the ratio of luciferase activity between Rluc regulated by a 5'-flanking PMP22 gene and hluc independent from a PMP22 gene was measured.

Figure 15:
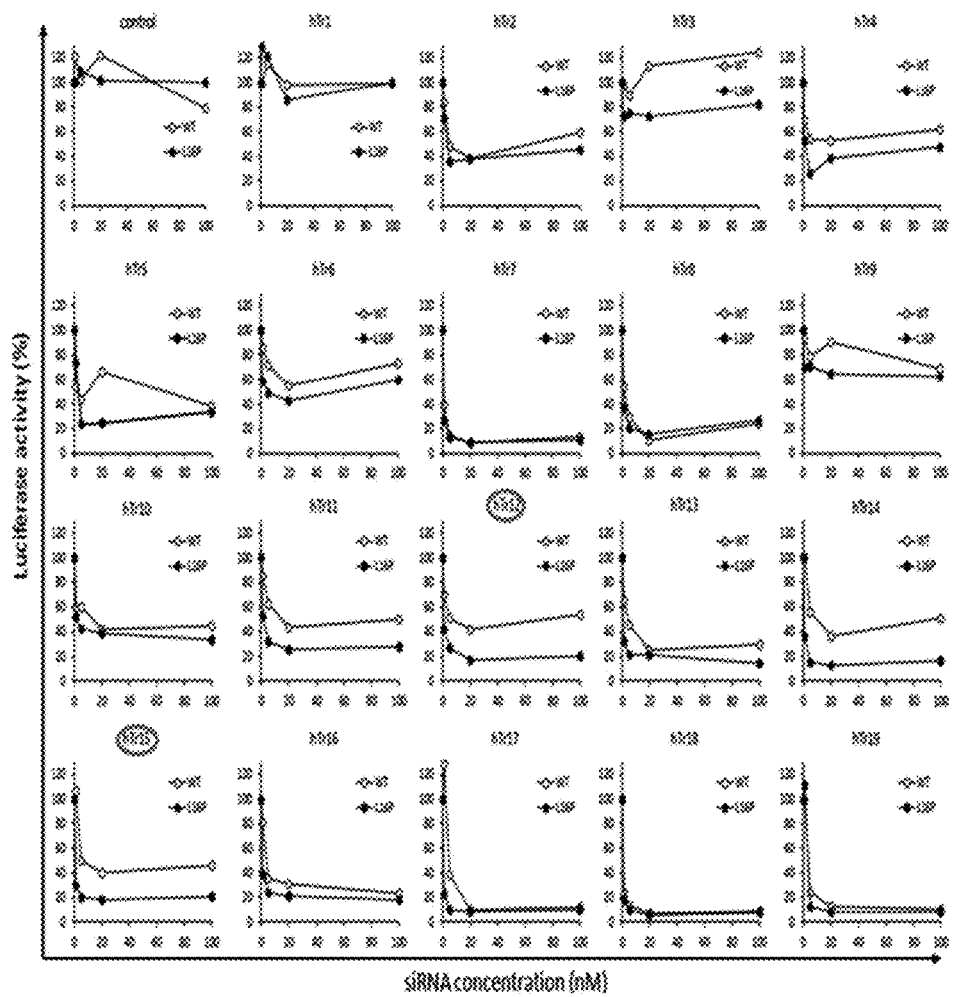
FIG. 15 shows results obtained by performing a dual-luciferase assay on 19 siRNAs to screen siRNAs specific to a human Pmp22-L16P mutant gene.

As a result, it was confirmed that the control-siRNA had no influence on either the wild-type PMP22 gene (WT) or the L16P mutant PMP22 gene, as shown in FIG. 15. Although most of the siRNAs targeting PMP22-L16P did not show allele-specificity, it was revealed that hTr12 (SEQ ID NO: 3) and hTr15 (SEQ ID NO: 4) suppressed the L16P mutant PMP22 gene by 72% and 80%, respectively, when present at a concentration of 5 nM. Further, it was revealed that the specificity of the siRNA to the mutant allele was clearly observed at a concentration of 100 nM.

According to the present invention, it was confirmed that the selective suppression of the PMP22 mutant allele by the non-viral delivery system of siRNA was able to improve demyelinating neuropathic symptoms of CMT in vivo, enhance a motor ability and increase a volume of muscle. Therefore, the siRNA can be used in a useful method for treating various dominantly inherited peripheral neuropathies including CMT.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of treating Charcot Marie Tooth disease in a subject in need thereof, comprising:
   administering to the subject an effective amount of a pharmaceutical composition comprising an expression inhibitor of a peripheral myelin protein 22 (PMP22) mutant gene as an active ingredient,
   wherein the expression inhibitor is a small interfering RNA (siRNA) haying a sense strand selected from the group consisting of SEQ ID NOs: 2, 3, and 4, and an antisense strand consisting of a sequence complementary to the sense strand.

2. The method of claim 1, wherein the PMP22 mutant gene is characterized by thymine, which is a base at position 47 of a wild-type PMP22 gene, being replaced with cytosine.

3. The method of claim 2, wherein the PMP22 mutant gene consists of a base sequence set forth in SEQ ID NO: 1.

4. The method of claim 1, wherein the composition further comprises a lipid polymer as an siRNA delivery system.

5. An siRNA having a sense strand selected from the group consisting of SEQ ID NOs: 2, 3, and 4 and an antisense strand consisting of a sequence complementary to the sense strand and binding to a PMP22 mutant gene to suppress expression of the PMP22 mutant gene.

6. The siRNA of claim 5, wherein the PMP22 mutant gene is characterized by thymine, which is a base at position 47 of a wild-type PMP22 gene, being replaced with cytosine.

7. The siRNA of claim 6, wherein the PMP22 mutant gene consists of a base sequence set forth in SEQ ID NO: 1.

8. A recombinant vector comprising the siRNA defined in claim 5.

9. A method of treating Charcot Marie Tooth disease in a subject in need thereof, comprising administering the siRNA of claim 5 to the subject.

10. A method of suppressing expression of a target gene in cells, comprising: introducing the siRNA of claim 5 into the cells in vitro.

11. The method of claim 10, wherein the target gene is a PMP22 mutant gene.

12. The method of claim 11, wherein the PMP22 mutant gene consists of a base sequence set forth in SEQ ID NO: 1.

* * * * *

SEQUENCE LISTING

<160> NUMBER OF SEQ ID NOS: 56

<210> SEQ ID NO 1
<211> LENGTH: 483
<212> TYPE: DNA
<213> ORGANISM: Homo sapiens
<220> FEATURE:
<221> NAME/KEY: gene
<222> LOCATION: (1)..(483)
<223> OTHER INFORMATION: hPMP22 L16P mutation gene

<400> SEQUENCE: 1

```
atgctcctcc tgttgctgag tatcatcgtc ctccacgtcg cggtgccggt gctgctgttc    60
gtctccacga tcgtcagcca atggatcgtg ggcaatggac acgcaactga tctctggcag   120
aactgtagca cctcttcctc aggaaatgtc caccactgtt tctcatcatc accaaacgaa   180
tggctgcagt ctgtccaggc caccatgatc ctgtcgatca tcttcagcat tctgtctctg   240
ttcctgttct tctgccaact cttcaccctc accaaggggg gcaggtttta catcactgga   300
atcttccaaa ttcttgctgg tctgtgcgtg atgagtgctg cggccatcta cacggtgagg   360
cacccggagt ggcatctcaa ctcggattac tcctacggtt tcgcctacat cctggcctgg   420
gtggccttcc ccctggccct tctcagcggt gtcatctatg tgatcttgcg gaaacgcgaa   480
tga                                                                 483
```

<210> SEQ ID NO 2
<211> LENGTH: 21
<212> TYPE: RNA
<213> ORGANISM: Artificial Sequence
<220> FEATURE:
<223> OTHER INFORMATION: mTr11 (siRNA)

<400> SEQUENCE: 2
cgcggugccg gugcugcugu u    21

<210> SEQ ID NO 3
<211> LENGTH: 21
<212> TYPE: RNA
<213> ORGANISM: Artificial Sequence
<220> FEATURE:
<223> OTHER INFORMATION: hTr12 (siRNA)

<400> SEQUENCE: 3
gcggugccgg ugcugcuguu u    21

<210> SEQ ID NO 4
<211> LENGTH: 21
<212> TYPE: RNA
<213> ORGANISM: Artificial Sequence
<220> FEATURE:
<223> OTHER INFORMATION: hTr15 (siRNA)

<400> SEQUENCE: 4
gugccggugc ugcuguucgu u    21

<210> SEQ ID NO 5
<211> LENGTH: 26
<212> TYPE: DNA
<213> ORGANISM: Artificial Sequence
<220> FEATURE:
<223> OTHER INFORMATION: Pmp22-L16P Forward Primer

<400> SEQUENCE: 5
atcgcggtgc cagtgttgct cttcgt    26

<210> SEQ ID NO 6
<211> LENGTH: 26
<212> TYPE: DNA
<213> ORGANISM: Artificial Sequence
<220> FEATURE:
<223> OTHER INFORMATION: Pmp22-L16P Reverse Primer

<400> SEQUENCE: 6
gagcaacact ggcaccgcga tgtgca                                  26

<210> SEQ ID NO 7
<211> LENGTH: 21
<212> TYPE: DNA
<213> ORGANISM: Artificial Sequence
<220> FEATURE:
<223> OTHER INFORMATION: Pmp22 Forward Primer

<400> SEQUENCE: 7
atggacacac gactgatctc t                                       21

<210> SEQ ID NO 8
<211> LENGTH: 21
<212> TYPE: DNA
<213> ORGANISM: Artificial Sequence
<220> FEATURE:
<223> OTHER INFORMATION: Pmp22 Reverse Primer

<400> SEQUENCE: 8
cagccattcg ctcactgatg a                                       21

<210> SEQ ID NO 9
<211> LENGTH: 21
<212> TYPE: DNA
<213> ORGANISM: Artificial Sequence
<220> FEATURE:
<223> OTHER INFORMATION: Mbp Forward Primer

<400> SEQUENCE: 9
gaccatccaa gaagacccca c                                       21

<210> SEQ ID NO 10
<211> LENGTH: 23
<212> TYPE: DNA
<213> ORGANISM: Artificial Sequence
<220> FEATURE:
<223> OTHER INFORMATION: Mbp Reverse Primer

<400> SEQUENCE: 10
gccataatgg gtagttctcg tgt                                     23

<210> SEQ ID NO 11
<211> LENGTH: 22
<212> TYPE: DNA
<213> ORGANISM: Artificial Sequence
<220> FEATURE:
<223> OTHER INFORMATION: Mpz Forward Primer

<400> SEQUENCE: 11
cggacaggga aatctatggt gc                                      22

<210> SEQ ID NO 12
<211> LENGTH: 22
<212> TYPE: DNA
<213> ORGANISM: Artificial Sequence
<220> FEATURE:

<223> OTHER INFORMATION: Mpz Reverse Primer

<400> SEQUENCE: 12
gcgccaggta aaagagatgt ca                                              22

<210> SEQ ID NO 13
<211> LENGTH: 22
<212> TYPE: DNA
<213> ORGANISM: Artificial Sequence
<220> FEATURE:
<223> OTHER INFORMATION: Actin Forward Primer

<400> SEQUENCE: 13
gtgacgttga catccgtaaa ga                                              22

<210> SEQ ID NO 14
<211> LENGTH: 19
<212> TYPE: DNA
<213> ORGANISM: Artificial Sequence
<220> FEATURE:
<223> OTHER INFORMATION: Actin Reverse Primer

<400> SEQUENCE: 14
gccggactca tcgtactcc                                                  19

<210> SEQ ID NO 15
<211> LENGTH: 49
<212> TYPE: DNA
<213> ORGANISM: Mus musculus

<400> SEQUENCE: 15
ctgttcctgc acatcgcggt gctagtgttg ctcttcgtct ccaccatcg                 49

<210> SEQ ID NO 16
<211> LENGTH: 49
<212> TYPE: DNA
<213> ORGANISM: Mus musculus

<400> SEQUENCE: 16
ctgttcctgc acatcgcggt gccagtgttg ctcttcgtct ccaccatcg                 49

<210> SEQ ID NO 17
<211> LENGTH: 21
<212> TYPE: DNA
<213> ORGANISM: Artificial Sequence
<220> FEATURE:
<223> OTHER INFORMATION: mTr1 siRNA
<220> FEATURE:
<221> NAME/KEY: misc_RNA
<222> LOCATION: (20)..(21)
<223> OTHER INFORMATION: deoxythymidine

<400> SEQUENCE: 17
uccugcacau cgcggugcct t                                               21

<210> SEQ ID NO 18
<211> LENGTH: 21
<212> TYPE: DNA
<213> ORGANISM: Artificial Sequence
<220> FEATURE:
<223> OTHER INFORMATION: mTr2
<220> FEATURE:
<221> NAME/KEY: misc_feature
<222> LOCATION: (20)..(21)
<223> OTHER INFORMATION: deoxythymidine

<400> SEQUENCE: 18
ccugcacauc gcggugccat t                    21

<210> SEQ ID NO 19
<211> LENGTH: 21
<212> TYPE: DNA
<213> ORGANISM: artificial sequence
<220> FEATURE:
<223> OTHER INFORMATION: mTr3 siRNA
<220> FEATURE:
<221> NAME/KEY: misc_feature
<222> LOCATION: (20)..(21)
<223> OTHER INFORMATION: deoxythymidine

<400> SEQUENCE: 19
cugcacaucg cggugccagt t                    21

<210> SEQ ID NO 20
<211> LENGTH: 21
<212> TYPE: DNA
<213> ORGANISM: Artificial Sequence
<220> FEATURE:
<223> OTHER INFORMATION: mTr4 siRNA
<220> FEATURE:
<221> NAME/KEY: misc_feature
<222> LOCATION: (20)..(21)
<223> OTHER INFORMATION: deoxythymidine

<400> SEQUENCE: 20
ugcacaucgc ggugccagut t                    21

<210> SEQ ID NO 21
<211> LENGTH: 21
<212> TYPE: DNA
<213> ORGANISM: artificial sequence
<220> FEATURE:
<223> OTHER INFORMATION: mTr5 siRNA
<220> FEATURE:
<221> NAME/KEY: misc_feature
<222> LOCATION: (20)..(21)
<223> OTHER INFORMATION: deoxythymidine

<400> SEQUENCE: 21
gcacaucgcg gugccagugt t                    21

<210> SEQ ID NO 22
<211> LENGTH: 21
<212> TYPE: DNA
<213> ORGANISM: Artificial Sequence
<220> FEATURE:
<223> OTHER INFORMATION: mTr6 siRNA
<220> FEATURE:
<221> NAME/KEY: misc_feature
<222> LOCATION: (20)..(21)
<223> OTHER INFORMATION: deoxythymidine

<400> SEQUENCE: 22
cacaucgcgg ugccagugut t                    21

<210> SEQ ID NO 23
<211> LENGTH: 21
<212> TYPE: DNA
<213> ORGANISM: Artificial Sequence
<220> FEATURE:
<223> OTHER INFORMATION: mTr7 siRNA
<220> FEATURE:
<221> NAME/KEY: misc_feature
<222> LOCATION: (20)..(21)
<223> OTHER INFORMATION: deoxythymidine

<400> SEQUENCE: 23
acaucgcggu gccaguguut t                                    21

<210> SEQ ID NO 24
<211> LENGTH: 21
<212> TYPE: DNA
<213> ORGANISM: artificial sequence
<220> FEATURE:
<223> OTHER INFORMATION: mTr8 siRNA
<220> FEATURE:
<221> NAME/KEY: misc_feature
<222> LOCATION: (20)..(21)
<223> OTHER INFORMATION: deoxythymidine

<400> SEQUENCE: 24
caucgcggug ccaguguugt t                                    21

<210> SEQ ID NO 25
<211> LENGTH: 21
<212> TYPE: DNA
<213> ORGANISM: artificial sequene
<220> FEATURE:
<223> OTHER INFORMATION: mTr9 siRNA
<220> FEATURE:
<221> NAME/KEY: misc_feature
<222> LOCATION: (20)..(21)
<223> OTHER INFORMATION: deoxythymidine

<400> SEQUENCE: 25
aucgcggugc caguguugct t                                    21

<210> SEQ ID NO 26
<211> LENGTH: 21
<212> TYPE: DNA
<213> ORGANISM: Artificial sequence
<220> FEATURE:
<223> OTHER INFORMATION: mTr10 siRNA
<220> FEATURE:
<221> NAME/KEY: misc_feature
<222> LOCATION: (20)..(21)
<223> OTHER INFORMATION: deoxythymidine

<400> SEQUENCE: 26
ucgcggugcc aguguugcut t                                    21

<210> SEQ ID NO 27
<211> LENGTH: 21
<212> TYPE: DNA
<213> ORGANISM: artificial sequence
<220> FEATURE:
<223> OTHER INFORMATION: mTr11 siRNA
<220> FEATURE:
<221> NAME/KEY: misc_feature
<222> LOCATION: (20)..(21)
<223> OTHER INFORMATION: deoxythymidine

<400> SEQUENCE: 27
cgcggugcca guguugcuct t                                    21

<210> SEQ ID NO 28
<211> LENGTH: 21
<212> TYPE: DNA
<213> ORGANISM: artificial sequence
<220> FEATURE:
<223> OTHER INFORMATION: mTr12 siRNA
<220> FEATURE:
<221> NAME/KEY: misc_feature
<222> LOCATION: (20)..(21)
<223> OTHER INFORMATION: deoxythymidine

<400> SEQUENCE: 28
gcggugccag uguugcucut t                                              21

<210> SEQ ID NO 29
<211> LENGTH: 21
<212> TYPE: DNA
<213> ORGANISM: artificial sequence
<220> FEATURE:
<223> OTHER INFORMATION: mTr13 siRNA
<220> FEATURE:
<221> NAME/KEY: misc_feature
<222> LOCATION: (20)..(21)
<223> OTHER INFORMATION: deoxythymidine

<400> SEQUENCE: 29
cggugccagu guugcucuut t                                              21

<210> SEQ ID NO 30
<211> LENGTH: 21
<212> TYPE: DNA
<213> ORGANISM: artificial sequence
<220> FEATURE:
<223> OTHER INFORMATION: mTr14 siRNA
<220> FEATURE:
<221> NAME/KEY: misc_feature
<222> LOCATION: (20)..(21)
<223> OTHER INFORMATION: deoxythymidine

<400> SEQUENCE: 30
ggugccagug uugcucuuct t                                              21

<210> SEQ ID NO 31
<211> LENGTH: 21
<212> TYPE: DNA
<213> ORGANISM: artificial sequence
<220> FEATURE:
<223> OTHER INFORMATION: mTr15 siRNA
<220> FEATURE:
<221> NAME/KEY: misc_feature
<222> LOCATION: (20)..(21)
<223> OTHER INFORMATION: deoxythymidine

<400> SEQUENCE: 31
gugccagugu ugcucuucgt t                                              21

<210> SEQ ID NO 32
<211> LENGTH: 21
<212> TYPE: DNA
<213> ORGANISM: Artificial Sequence
<220> FEATURE:
<223> OTHER INFORMATION: mTr16 siRNA
<220> FEATURE:
<221> NAME/KEY: misc_feature
<222> LOCATION: (20)..(21)
<223> OTHER INFORMATION: deoxythymidine

<400> SEQUENCE: 32
ugccaguguu gcucuucgut t                                              21

<210> SEQ ID NO 33
<211> LENGTH: 21
<212> TYPE: DNA
<213> ORGANISM: artificial sequence
<220> FEATURE:
<223> OTHER INFORMATION: mTr17 siRNA
<220> FEATURE:
<221> NAME/KEY: misc_feature
<222> LOCATION: (20)..(21)

```
<223> OTHER INFORMATION: deoxythymidine

<400> SEQUENCE: 33
gccaguguug cucuucguct t                                              21

<210> SEQ ID NO 34
<211> LENGTH: 21
<212> TYPE: DNA
<213> ORGANISM: artificial sequence
<220> FEATURE:
<223> OTHER INFORMATION: mTr18 siRNA
<220> FEATURE:
<221> NAME/KEY: misc_feature
<222> LOCATION: (20)..(21)
<223> OTHER INFORMATION: deoxythymidine

<400> SEQUENCE: 34
ccaguguugc ucuucgucut t                                              21

<210> SEQ ID NO 35
<211> LENGTH: 21
<212> TYPE: DNA
<213> ORGANISM: artificial sequence
<220> FEATURE:
<223> OTHER INFORMATION: mTr19 siRNA
<220> FEATURE:
<221> NAME/KEY: misc_feature
<222> LOCATION: (20)..(21)
<223> OTHER INFORMATION: deoxythymidine

<400> SEQUENCE: 35
caguguugcu cuucgucuct t                                              21

<210> SEQ ID NO 36
<211> LENGTH: 49
<212> TYPE: DNA
<213> ORGANISM: Homo sapiens

<400> SEQUENCE: 36
catcgtcctc cacgtcgcgg tgctggtgct gctgttcgtc tccacgatc                49

<210> SEQ ID NO 37
<211> LENGTH: 49
<212> TYPE: DNA
<213> ORGANISM: homo sapiens

<400> SEQUENCE: 37
catcgtcctc cacgtcgcgg tgccggtgct gctgttcgtc tccacgatc                49

<210> SEQ ID NO 38
<211> LENGTH: 21
<212> TYPE: DNA
<213> ORGANISM: artificial sequence
<220> FEATURE:
<223> OTHER INFORMATION: hTr1 siRNA
<220> FEATURE:
<221> NAME/KEY: misc_feature
<222> LOCATION: (20)..(21)
<223> OTHER INFORMATION: deoxythymidine

<400> SEQUENCE: 38
uccuccacgu cgcggugcct t                                              21

<210> SEQ ID NO 39
<211> LENGTH: 21
<212> TYPE: DNA
<213> ORGANISM: artificial sequence
```

```
<220> FEATURE:
<223> OTHER INFORMATION: hTr2 siRNA
<220> FEATURE:
<221> NAME/KEY: misc_feature
<222> LOCATION: (20)..(21)
<223> OTHER INFORMATION: deoxythymidine

<400> SEQUENCE: 39
ccuccacguc gcggugccgt t                                              21

<210> SEQ ID NO 40
<211> LENGTH: 21
<212> TYPE: DNA
<213> ORGANISM: artificial sequence
<220> FEATURE:
<223> OTHER INFORMATION: hTr3 siRNA
<220> FEATURE:
<221> NAME/KEY: misc_feature
<222> LOCATION: (20)..(21)
<223> OTHER INFORMATION: deoxythymidine

<400> SEQUENCE: 40
cuccacgucg cggugccggt t                                              21

<210> SEQ ID NO 41
<211> LENGTH: 21
<212> TYPE: DNA
<213> ORGANISM: artificial sequence
<220> FEATURE:
<223> OTHER INFORMATION: hTr4 siRNA
<220> FEATURE:
<221> NAME/KEY: misc_feature
<222> LOCATION: (20)..(21)
<223> OTHER INFORMATION: deoxythymidine

<400> SEQUENCE: 41
uccacgucgc ggugccggut t                                              21

<210> SEQ ID NO 42
<211> LENGTH: 21
<212> TYPE: DNA
<213> ORGANISM: artificial sequence
<220> FEATURE:
<223> OTHER INFORMATION: hTr5 siRNA
<220> FEATURE:
<221> NAME/KEY: misc_feature
<222> LOCATION: (20)..(21)
<223> OTHER INFORMATION: deoxythymidine

<400> SEQUENCE: 42
ccacgucgcg gugccggugt t                                              21

<210> SEQ ID NO 43
<211> LENGTH: 21
<212> TYPE: DNA
<213> ORGANISM: artificial sequence
<220> FEATURE:
<223> OTHER INFORMATION: hTr6 siRNA
<220> FEATURE:
<221> NAME/KEY: misc_feature
<222> LOCATION: (20)..(21)
<223> OTHER INFORMATION: deoxythymidine

<400> SEQUENCE: 43
cacgucgcgg ugccggugct t                                              21

<210> SEQ ID NO 44
<211> LENGTH: 21
<212> TYPE: DNA
```

```
<213> ORGANISM: artificial sequence
<220> FEATURE:
<223> OTHER INFORMATION: hTr7 siRNA
<220> FEATURE:
<221> NAME/KEY: misc_feature
<222> LOCATION: (20)..(21)
<223> OTHER INFORMATION: deoxythymidine

<400> SEQUENCE: 44
acgucgcggu gccggugcut t                                              21

<210> SEQ ID NO 45
<211> LENGTH: 21
<212> TYPE: DNA
<213> ORGANISM: artificial sequence
<220> FEATURE:
<223> OTHER INFORMATION: hTr8 siRNA
<220> FEATURE:
<221> NAME/KEY: misc_feature
<222> LOCATION: (20)..(21)
<223> OTHER INFORMATION: deoxythymidine

<400> SEQUENCE: 45
cgucgcggug ccggugcugt t                                              21

<210> SEQ ID NO 46
<211> LENGTH: 21
<212> TYPE: DNA
<213> ORGANISM: artificial sequence
<220> FEATURE:
<223> OTHER INFORMATION: hTr9 siRNA
<220> FEATURE:
<221> NAME/KEY: misc_feature
<222> LOCATION: (20)..(21)
<223> OTHER INFORMATION: deoxythymidine

<400> SEQUENCE: 46
gucgcggugc cggugcugct t                                              21

<210> SEQ ID NO 47
<211> LENGTH: 21
<212> TYPE: DNA
<213> ORGANISM: artificial sequence
<220> FEATURE:
<223> OTHER INFORMATION: hTr10 siRNA
<220> FEATURE:
<221> NAME/KEY: misc_feature
<222> LOCATION: (20)..(21)
<223> OTHER INFORMATION: deoxythymidine

<400> SEQUENCE: 47
ucgcggugcc ggugcugcut t                                              21

<210> SEQ ID NO 48
<211> LENGTH: 21
<212> TYPE: DNA
<213> ORGANISM: artificial sequence
<220> FEATURE:
<223> OTHER INFORMATION: hTr11 siRNA
<220> FEATURE:
<221> NAME/KEY: misc_feature
<222> LOCATION: (20)..(21)
<223> OTHER INFORMATION: deoxythymidine

<400> SEQUENCE: 48
cgcggugccg gugcugcugt t                                              21

<210> SEQ ID NO 49
<211> LENGTH: 21
```

```
<212> TYPE: DNA
<213> ORGANISM: artificial sequence
<220> FEATURE:
<223> OTHER INFORMATION: hTr12 siRNA
<220> FEATURE:
<221> NAME/KEY: misc_feature
<222> LOCATION: (20)..(21)
<223> OTHER INFORMATION: deoxythymidine

<400> SEQUENCE: 49
gcggugccgg ugcugcugut t                                              21

<210> SEQ ID NO 50
<211> LENGTH: 21
<212> TYPE: DNA
<213> ORGANISM: artificial sequence
<220> FEATURE:
<223> OTHER INFORMATION: hTr13 siRNA
<220> FEATURE:
<221> NAME/KEY: misc_feature
<222> LOCATION: (20)..(21)
<223> OTHER INFORMATION: deoxythymidine

<400> SEQUENCE: 50
cggugccggu gcugcuguut t                                              21

<210> SEQ ID NO 51
<211> LENGTH: 21
<212> TYPE: DNA
<213> ORGANISM: artificial sequence
<220> FEATURE:
<223> OTHER INFORMATION: hTr14 siRNA
<220> FEATURE:
<221> NAME/KEY: misc_feature
<222> LOCATION: (20)..(21)
<223> OTHER INFORMATION: deoxythymidine

<400> SEQUENCE: 51
ggugccggug cugcuguuct t                                              21

<210> SEQ ID NO 52
<211> LENGTH: 21
<212> TYPE: DNA
<213> ORGANISM: artificial sequence
<220> FEATURE:
<223> OTHER INFORMATION: hTr15 siRNA

<400> SEQUENCE: 52
gugccggugc ugcuguucgt t                                              21

<210> SEQ ID NO 53
<211> LENGTH: 21
<212> TYPE: DNA
<213> ORGANISM: artificial sequence
<220> FEATURE:
<223> OTHER INFORMATION: hTr16 siRNA
<220> FEATURE:
<221> NAME/KEY: misc_feature
<222> LOCATION: (20)..(21)
<223> OTHER INFORMATION: deoxythymidine

<400> SEQUENCE: 53
ugccggugcu gcuguucgut t                                              21

<210> SEQ ID NO 54
<211> LENGTH: 21
<212> TYPE: DNA
<213> ORGANISM: artificial sequence
<220> FEATURE:
```

```
<223> OTHER INFORMATION: hTr17 siRNA
<220> FEATURE:
<221> NAME/KEY: misc_feature
<222> LOCATION: (20)..(21)
<223> OTHER INFORMATION: deoxythymidine

<400> SEQUENCE: 54
gccggugcug cguucguct t                                                  21

<210> SEQ ID NO 55
<211> LENGTH: 21
<212> TYPE: DNA
<213> ORGANISM: artificial sequence
<220> FEATURE:
<223> OTHER INFORMATION: hTr18 siRNA
<220> FEATURE:
<221> NAME/KEY: misc_feature
<222> LOCATION: (20)..(21)
<223> OTHER INFORMATION: deoxythymidine

<400> SEQUENCE: 55
ccggugcugc uguucgucut t                                                 21

<210> SEQ ID NO 56
<211> LENGTH: 21
<212> TYPE: DNA
<213> ORGANISM: artificial sequence
<220> FEATURE:
<223> OTHER INFORMATION: hTr19 siRNA
<220> FEATURE:
<221> NAME/KEY: misc_feature
<222> LOCATION: (20)..(21)
<223> OTHER INFORMATION: deoxythymidine

<400> SEQUENCE: 56
cggugcugcu guucgucuct t                                                 21
```